United States Patent
Rao et al.

(10) Patent No.: US 10,465,218 B2
(45) Date of Patent: Nov. 5, 2019

(54) METHOD FOR INCREASING YIELD OF L-ARGININE BY KNOCKING OUT FLAVIN REDUCTASES

(71) Applicant: Jiangnan University, Wuxi (CN)

(72) Inventors: Zhiming Rao, Wuxi (CN); Zaiwei Man, Wuxi (CN); Meijuan Xu, Wuxi (CN); Taowei Yang, Wuxi (CN); Xian Zhang, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 0 days.

(21) Appl. No.: 16/063,639

(22) PCT Filed: Jul. 29, 2016

(86) PCT No.: PCT/CN2016/092179
§ 371 (c)(1),
(2) Date: Jun. 18, 2018

(87) PCT Pub. No.: WO2018/018569
PCT Pub. Date: Feb. 1, 2018

(65) Prior Publication Data
US 2019/0153489 A1    May 23, 2019

(30) Foreign Application Priority Data
Jul. 26, 2016 (CN) .......................... 2016 1 0592588

(51) Int. Cl.
| C12N 9/06 | (2006.01) |
| C12N 1/20 | (2006.01) |
| C12Q 1/68 | (2018.01) |
| C12P 13/10 | (2006.01) |
| C07H 21/04 | (2006.01) |
| C12N 15/09 | (2006.01) |

(52) U.S. Cl.
CPC ............ *C12P 13/10* (2013.01); *C12N 9/0028* (2013.01); *C12N 15/09* (2013.01); *C12Y 105/01038* (2013.01)

(58) Field of Classification Search
None
See application file for complete search history.

(56) References Cited

PUBLICATIONS

Man. Improvement of the intracellular environment for enhancing L-arginine production of Corynebacterium glutamicum by inactivation of H2O2-forming flavin reductases and optimization of ATP supply. Metabolic Engineering 38 (2016) 310-321.*
Xu. A two-stage oxygen supply strategy for enhanced l-arginine production by Corynebacterium crenatum based on metabolic fluxes analysis. Biochemical Engineering Journal 43 (2009) 41-51.*
Man. Systems pathway engineering of Corynebacterium crenatum for improved L-arginine production Scientific Reports | 6:28629. Mar. 2016.*
Hertzberger. H2O2 Production in Species of the Lactobacillus acidophilus Group: a Central Role for a Novel NADH-Dependent Flavin Reductase. Applied and Environmental Microbiology p. 2229-2239. vol. 80, No. 7, 2014.*
Chen (ROJC147—UnitProtKB database. 2013.*
Ahn (A0AF6Z5D9—UniProtKB database. 2015.*
Hertzberger Ry et. al., Oxygen Relieves the CO2 and Acetate Dependency of Lactobacillus johnsonii NCC 533, PLOS ONE, Feb. 2013, vol 8, Issue 2, e57235.
Bringel F et. al.,Arginine Biosynthesis and Regulation in Lactobacillus plantarum: the carA Gene and the argCJBDF Cluster Are Divergently Transcribed,Journal of Bacteriology, vol. 179 No. 8,Apr. 1997, p. 2697-2706.

* cited by examiner

*Primary Examiner* — Yong D Pak
(74) *Attorney, Agent, or Firm* — IPro, PLLC; Na Xu; Qian Gu

(57) ABSTRACT

The invention discloses a method for increasing the yield of L-arginine by knocking out flavin reductases, and belongs to the technical field of amino acid production by microbial fermentation. Genes frd1 and frd2 for encoding hypothetic NADPH-dependent FMN reductase in *Corynebacterium crenatum* SDNN403 are over-expressed in *E. coli* BL21 and are purified to form target proteins Frd181 and Frd188, and functions of the target proteins are identified to obtain a result showing that the proteins Frd181 and Frd188 both are NAD(P)H-dependent flavin reductases producing $H_2O_2$. By taking a genome of the *Corynebacterium crenatum* SDNN403 as a template, frd1 and frd2 gene deletion fragments are obtained by overlap extension PCR; connecting pK18mobsacB to obtain knockout plasmids pK18mobsacB-Δfrd1 and pK18mobsacB-Δfrd2; carrying out electric shock to transform the *Corynebacterium crenatum* SDNN403; and carrying out secondary screening to obtain recombinant strains 403Δfrd1 and 403Δfrd2. Found by flask shaking fermentation, the yield of L-arginine is obviously increased by knocking out the genes frd1 and frd2.

10 Claims, No Drawings
Specification includes a Sequence Listing.

SEQUENCE LISTING

```
<160> NUMBER OF SEQ ID NOS: 16

<210> SEQ ID NO 1
<211> LENGTH: 546
<212> TYPE: DNA
<213> ORGANISM: Artificial Sequence
<220> FEATURE:
<223> OTHER INFORMATION: Synthetic DNA

<400> SEQUENCE: 1
atgaaaatcg gcgtcattct aggaagtatc cgcgagggtc ggttcggtgc aggtgttgcc        60
gattgggtca tggaacaagt cgcagcatat gctgccccg atgcggagtt tgaactccta       120
gaccttaaat ctttcaatgt tccactgttg gaatccgcca ctgttccagg tgctgccaac       180
aaacaatacg acgatccgca ggtcactgcc tggtctaaag ccatcgatgc ctgtgacgcc       240 tttatttttca tcacccccga gtacaaccac ggtgtacccg gcgcgttcaa aaatgccttc       300
gatgtcttag gcaatgagtg gcaaaacaaa gttgtcgctt tcgtttccta tggtgcagct       360
gaaggtgtcc gtgctgttga gcagtggcgc caaattgtcg gaaacttcaa tattttgat        420 atccgcagcc aggtaacttt ttccaccttc actgaaaata aagacggcgc gtttagcccc       480
aacgaacgcc gcgccggtga attagacagg ctgcttgaca gcctcctaac ggctgtccgc       540
gattaa                                                                 546

<210> SEQ ID NO 2
<211> LENGTH: 181
<212> TYPE: PRT
<213> ORGANISM: Artificial Sequence
<220> FEATURE:
<223> OTHER INFORMATION: Protein translated from Synthetic DNA

<400> SEQUENCE: 2
```

```
Met Lys Ile Gly Val Ile Leu Gly Ser Ile Arg Gly Arg Phe Gly
1               5                   10                  15

Ala Gly Val Ala Asp Trp Val Met Glu Gln Val Ala Ala Tyr Ala Ala
            20                  25                  30

Pro Asp Ala Glu Phe Glu Leu Leu Asp Leu Lys Ser Phe Asn Val Pro
            35                  40                  45

Leu Leu Glu Ser Ala Thr Val Pro Gly Ala Ala Asn Lys Gln Tyr Asp
50                  55                  60

Asp Pro Gln Val Thr Ala Trp Ser Lys Ala Ile Asp Ala Cys Asp Ala
65                  70                  75                  80

Phe Ile Phe Ile Thr Pro Glu Tyr Asn His Gly Val Pro Gly Ala Phe
                85                  90                  95

Lys Asn Ala Phe Asp Val Leu Gly Asn Glu Trp Gln Asn Lys Val Val
                100                 105                 110

Ala Phe Val Ser Tyr Gly Ala Ala Glu Gly Val Arg Ala Val Glu Gln
            115                 120                 125

Trp Arg Gln Ile Val Gly Asn Phe Asn Ile Phe Asp Ile Arg Ser Gln
            130                 135                 140

Val Thr Phe Ser Thr Phe Thr Glu Asn Lys Asp Gly Ala Phe Ser Pro
145                 150                 155                 160

Asn Glu Arg Arg Ala Gly Glu Leu Asp Arg Leu Leu Asp Ser Leu Leu
                165                 170                 175

Thr Ala Val Arg Asp
            180

<210> SEQ ID NO 3
<211> LENGTH: 567
<212> TYPE: DNA
<213> ORGANISM: Artificial Sequence
<220> FEATURE:
<223> OTHER INFORMATION: Synthetic DNA

<400> SEQUENCE: 3
atgagcaaga tcgccatcat caccggttcc acccgcccag gccgcgtcaa cattgacgta      60
gccaactggg ttctcgagcg cgcacaagag cgcaacgatg cacagtacga gctcgttgat     120
atcgccgatt tcaacttccc cgtcctcgac gaagcaatgc cagccggcta cggccagtat     180
gcaaacgagc acaccaaggc atgggcagca agatcgcag aatttgatgg cttcatcttt     240
gttaccggcg aatacaacca ctccgtccca gcagcactaa ccaacgccct ttcctacctc     300
tccgcagagt ggaacaacaa ggctgcaggc atcgtctcct acggctccgc aatgggcgtt     360
cgcgcagctg agcacctccg cggcatcctt ccgagcttc agatcgcaca cgttcaaaag     420
accggcctgc tgagcatctt caccgacttc gaatacccta acttcaagcc ttccgagcag     480
ggcatctcct ctgtggacgc tatgcttgag cagcttgttg tctggaccaa ggcaatgtcc     540
accattcgtg agtctgcaaa cgtctaa                                        567

<210> SEQ ID NO 4
<211> LENGTH: 188
<212> TYPE: PRT
<213> ORGANISM: Artificial Sequence
<220> FEATURE:
<223> OTHER INFORMATION: Protein translated from Synthetic DNA

<400> SEQUENCE: 4

Met Ser Lys Ile Ala Ile Ile Thr Gly Ser Thr Arg Pro Gly Arg Val
1               5                   10                  15
```

Asn Ile Asp Val Ala Asn Trp Val Leu Glu Arg Ala Gln Glu Arg Asn
            20                  25                  30

Asp Ala Gln Tyr Glu Leu Val Asp Ile Ala Asp Phe Asn Phe Pro Val
        35                  40                  45

Leu Asp Glu Ala Met Pro Ala Gly Tyr Gly Gln Tyr Ala Asn Glu His
50                  55                  60

Thr Lys Ala Trp Ala Ala Lys Ile Ala Glu Phe Asp Gly Phe Ile Phe
65                  70                  75                  80

Val Thr Gly Glu Tyr Asn His Ser Val Pro Ala Ala Leu Thr Asn Ala
                85                  90                  95

Leu Ser Tyr Leu Ser Ala Glu Trp Asn Asn Lys Ala Ala Gly Ile Val
            100                 105                 110

Ser Tyr Gly Ser Ala Met Gly Val Arg Ala Ala Glu His Leu Arg Gly
        115                 120                 125

Ile Leu Ser Glu Leu Gln Ile Ala His Val Gln Lys Thr Gly Leu Leu
130                 135                 140

Ser Ile Phe Thr Asp Phe Glu Tyr Pro Asn Phe Lys Pro Ser Glu Gln
145                 150                 155                 160

Gly Ile Ser Ser Val Asp Ala Met Leu Glu Gln Leu Val Val Trp Thr
                165                 170                 175

Lys Ala Met Ser Thr Ile Arg Glu Ser Ala Asn Val
            180                 185

<210> SEQ ID NO 5
<211> LENGTH: 31
<212> TYPE: DNA
<213> ORGANISM: Artificial Sequence
<220> FEATURE:
<223> OTHER INFORMATION: Synthetic DNA

<400> SEQUENCE: 5
ccggaattca tgaaaatcgg cgtcattcta g         31

<210> SEQ ID NO 6
<211> LENGTH: 35
<212> TYPE: DNA
<213> ORGANISM: Artificial Sequence
<220> FEATURE:
<223> OTHER INFORMATION: Synthetic DNA

<400> SEQUENCE: 6
ccgctcgagt taatcgcgga cagccgttag gaggc      35

<210> SEQ ID NO 7
<211> LENGTH: 32
<212> TYPE: DNA
<213> ORGANISM: Artificial Sequence
<220> FEATURE:
<223> OTHER INFORMATION: Synthetic DNA

<400> SEQUENCE: 7
ccggaattca tgagcaagat cgccatcatc ac         32

<210> SEQ ID NO 8
<211> LENGTH: 27
<212> TYPE: DNA
<213> ORGANISM: Artificial Sequence
<220> FEATURE:
<223> OTHER INFORMATION: Synthetic DNA

<400> SEQUENCE: 8
cccaagcttt tagacgtttg cagactc                                              27

<210> SEQ ID NO 9
<211> LENGTH: 31
<212> TYPE: DNA
<213> ORGANISM: Artificial Sequence
<220> FEATURE:
<223> OTHER INFORMATION: Synthetic DNA

<400> SEQUENCE: 9
ccggaattca tgaaaatcgg cgtcattcta g                                         31

<210> SEQ ID NO 10
<211> LENGTH: 23
<212> TYPE: DNA
<213> ORGANISM: Artificial Sequence
<220> FEATURE:
<223> OTHER INFORMATION: Synthetic DNA

<400> SEQUENCE: 10
gttggcagca cctggaacag tgg                                                  23

<210> SEQ ID NO 11
<211> LENGTH: 47
<212> TYPE: DNA
<213> ORGANISM: Artificial Sequence
<220> FEATURE:
<223> OTHER INFORMATION: Synthetic DNA

<400> SEQUENCE: 11
ccactgttcc aggtgctgcc aacgaaggtg tccgtgctgt tgagcag                         47

<210> SEQ ID NO 12
<211> LENGTH: 36
<212> TYPE: DNA
<213> ORGANISM: Artificial Sequence
<220> FEATURE:
<223> OTHER INFORMATION: Synthetic DNA

<400> SEQUENCE: 12
ctagtctaga ttaatcgcgg acagccgtta ggaggc                                    36

<210> SEQ ID NO 13
<211> LENGTH: 32
<212> TYPE: DNA
<213> ORGANISM: Artificial Sequence
<220> FEATURE:
<223> OTHER INFORMATION: Synthetic DNA

<400> SEQUENCE: 13
ccggaattca tgagcaagat cgccatcatc ac                                        32

<210> SEQ ID NO 14
<211> LENGTH: 19
<212> TYPE: DNA
<213> ORGANISM: Artificial Sequence
<220> FEATURE:
<223> OTHER INFORMATION: Synthetic DNA

<400> SEQUENCE: 14
ctggcattgc ttcgtcgag                                                       19

<210> SEQ ID NO 15
<211> LENGTH: 35
<212> TYPE: DNA

-continued

```
<213> ORGANISM: Artificial Sequence
<220> FEATURE:
<223> OTHER INFORMATION: Synthetic DNA

<400> SEQUENCE: 15
ctcgacgaag caatgccagc agatcgcaca cgttc                          35

<210> SEQ ID NO 16
<211> LENGTH: 27
<212> TYPE: DNA
<213> ORGANISM: Artificial Sequence
<220> FEATURE:
<223> OTHER INFORMATION: Synthetic DNA

<400> SEQUENCE: 16
cccaagcttt tagacgtttg cagactc                                   27
```

METHOD FOR INCREASING YIELD OF L-ARGININE BY KNOCKING OUT FLAVIN REDUCTASES

TECHNICAL FIELD

The disclosure herein relates to the field of fermentain engineering, and more particularly relates to a method for increasing the yield of L-arginine by knocking out flavin reductases.

BACKGROUND

L-arginine is a semi-essential amino acid in human and animal bodies, is a synthesis precursor of various bioactive substances, and has various unique physiological and pharmacologic effects. With the continuous deep research and understanding of the biological function of arginine, arginine is more and more widely applied to medicines, food and feed industry.

Production methods of L-arginine include a hydrolysis method and a fermentation method. Currently, a protein hydrolysis method is still mainly adopted by most of existing manufacturers to produce L-arginine in China, and the method is serious in environment pollution and not high in yield, so as not to be suitable for large-scale production. The fermentation method for producing L-arginine is relatively simple in process and environment-friendly, so as to have a great development potential. However, a method for producing L-arginine by microbial fermentation domestically is generally relatively low in acid production level and relatively high in cost, and the production level and the yield cannot meet domestic demands. Therefore, it is very important to improve the fermentation acid production level of L-arginine and increase the utilization ratio of glucose.

*Corynebacterium crenatum* SDNN403 (the strain with a collection number of CGMCC NO:0890 and a patent number of ZL 03112896.3 is researched for many years by the research group, and is obtained by using a traditional mutagenesis method) is high-yield L-arginine *C. crenatum*. The anabolic pathway of L-arginine of the strain is systematically analyzed in preliminary work. The effect on regulating feedback inhibition and feedback repression in anabolism of L-arginine is researched to relieve feedback inhibition in the strain. Meanwhile, key metabolizing enzyme genes on a competition bypath for synthesizing arginine are subjected to metabolic transformation such as knockout, so that metabolic flows on competition branch pathways of proline, glutamine and the like are weakened while the expression of a key enzyme gene cluster on a synthesis pathway of arginine serving as a target product is enhanced, finally, the catabiosis of L-arginine is concentrated on an anabolic flow of L-arginine, and furthermore, the yield of arginine is increased.

Active oxygen comprises superoxide anions $O^{2-}$, hydroxyl radicals OH., hydrogen peroxide $H_2O_2$ and the like which are by-products in a biological aerobic metabolism process, and have very high toxicity for cells. After evolving for a long term, the cells have formed a set of action system for resisting the toxicity of active oxygen, for example, superoxide dismutase can be used for converting the superoxide anions $O^{2-}$ into $H_2O_2$, and catalase can be used for decomposing $H_2O_2$ into $H_2O$ and $O_2$. It is a passive defense process that the cells are decomposed after generating active oxygen, it is impossible to immediately eliminate produced active oxygen, and a small amount of active oxygen can still react with intracellular substances to damage the cells. If the synthesis of active oxygen can be directly reduced, the damage of active oxygen to the cells can be fundamentally reduced.

As one of active oxygen in the cells, $H_2O_2$ has very high oxidation activity and toxicity. It is reported that flavin reductases can be used for reducing oxidized flavins FMN and FAD as well as riboflavin into reduced flavins FMNH2 and FADH2 as well as reduced riboflavin by utilizing NAD(P)H, and then further carrying out catalysis to transfer electrons of reduced flavins to other intracellular electron acceptors. If the electron acceptors are $O_2$, it is possible to produce $H_2O_2$.

Found by retrieving a genome of *Corynebacterium glutamicum* ATCC13032, hypothetic NADPH-dependent FMN reductase is encoded by a gene cg1150 (genome NCBI Accession Number: BX927151) and a gene cg3223 (genome NCBI Accession Number: BX927156). However, functions of the two genes are not clear so far, and no correlated researches are reported.

Although it has been reported currently that the metabolic pathway of the strain is transformed to increase the yield of L-arginine, it is necessary to develop a novel method to further promote the synthesis of L-arginine.

SUMMARY

In order to solve the foregoing problem, the invention provides a method for increasing the yield of L-arginine. Hypothetic NADPH-dependent FMN reductase is identified, a final catalysate of the hypothetic NADPH-dependent FMN reductase is analyzed, and finally, the growth of a thallus and the synthesis of L-arginine are promoted by knocking out hypothetic NADPH-dependent FMN reductase gene(s) frd1 and/or frd2 in *C. crenatum*.

The first objective of the invention is to provide an L-arginine-yield-increased recombinant strain of *Corynebacterium crenatum*, and the recombinant strain is *Corynebacterium crenatum* in which NADPH-dependent FMN reductase gene(s) frd1 and/or frd2 are/is deleted.

In a mode of execution of the invention, an amino acid sequence of the NADPH-dependent FMN reductase gene frd1 is shown as SEQ ID NO.2, and a nucleotide sequence of the NADPH-dependent FMN reductase gene frd1 is shown as SEQ NO.1.

In a mode of execution of the invention, an amino acid sequence of the NADPH-dependent FMN reductase gene frd2 is shown as SEQ NO.4, and a nucleotide sequence of the NADPH-dependent FMN reductase gene frd2 is shown as SEQ ID NO.3.

In a mode of execution of the invention, the *Corynebacterium crenatum* is obtained by knocking out NADPH-dependent FMN reductase genes in *Corynebacterium crenatum* CGMCC NO:0890.

In a mode of execution of the invention, a construction method of the recombinant strain of the *Corynebacterium crenatum* comprises: obtaining frd1 and/or frd2 gene deletion fragments by taking a genome of the *Corynebacterium crenatum* CGMCC NO:0890 as a template, then, connecting obtained frd1 and/or frd2 gene deletion fragments with pK18mobsacB linearized vectors, shifting into *E. coli*, selecting positive transformants, and constructing plasmids pK18mobsacB-Δfrd1 and/or pK18mobsacB-Δfrd2; and carrying out electric shock on the plasmids pK18mobsacB-Δfrd1 and/or pK18mobsacB-Δfrd2 to transform *Corynebacterium crenatum* CGMCC NO:0890, firstly, carrying out culture on a solid culture medium plate containing kanamycin to obtain first homologous recombinant transformants, then, respectively carrying out forced secondary recombination screening on target transformants in a culture medium containing saccharose, identifying second homologous recombinant transformants, and naming strains identified to be correct as 403Δfrd1, 403Δfrd2 and 403Δfrd12.

The second objective of the invention is to provide a method for synthesizing L-arginine, and the method is fermentation culture by taking the recombinant strain of the *Corynebacterium crenatum* of any one of claims 1-5 as a production strain.

In a mode of execution of the invention, the fermentation is carried out at 28-32° C.

In a mode of execution of the invention, fermentation culture medium fermentation components: 120 g·L$^{-1}$ of glucose, 40 g·L$^{-1}$ of corn steep liquor, 8*10-5 g·L$^{-1}$ of biotin, 5*10-4 g·L$^{-1}$ of histidine, 0.02 g·L$^{-1}$ of manganese sulfate, 20 g·L$^{-1}$ of ammonium sulfate, 0.5 g·L$^{-1}$ of magnesium sulfate, 1.5 g·L$^{-1}$ of monopotassium phosphate and 0.02 g·L$^{-1}$ of ferrous sulfate.

The third objective of the invention is to provide a method for promoting the synthesis of L-arginine by knocking out flavin reductases, and the method comprises knocking out NADPH-dependent FMN reductase genes of *Corynebacterium crenatum* to obtain a recombinant strain, and synthesizing L-arginine by taking the recombinant strain as a production strain.

In a mode of execution of the invention, amino acid sequences of the NADPH-dependent FMN reductase genes frd1 and frd2 are respectively shown as SEQ ID NO.2 and SEQ NO.4.

The *Corynebacterium crenatum* is *Corynebacterium crenatum* CGMCC NO:0890.

The fourth objective of the invention is to provide L-arginine produced by using the recombinant strain and application of the recombinant strain to medicines, food or feed industry.

The yield of L-arginine produced by using the strain can be respectively increased by 16.46% and 3.16% by knocking out the gene frd1 or frd2, and the yield of L-arginine is respectively 18.4 g·L$^{-1}$ and 16.3 g·L$^{-1}$ after the recombinant strains 403Δfrd1 and 403Δfrd2 are fermented for 60 h.

DETAILED DESCRIPTION

For A strain used by the invention was *Corynebacterium crenatum* SDNN403, was a mutant strain for high-yield arginine obtained by laboratory screening, had a collection number of CGMCC NO.0890, had been disclosed in a patent document with a patent number of ZL 03112896.3, and was a known biological material.

Example 1: Purification and Functional Identification of Hypothetic NADPH-Dependent FMN Reductases Frd181 and Frd188

Hypothetic NADPH-dependent FMN reductases Frd181 and Frd188 were subjected to over-expression, purification and functional identification by an inventor. The specific steps were as follows:

Over-Expression and Purification

By taking a genome of *C. crenatum* SDNN403 (namely *Corynebacterium crenatum* CGMCC NO.0890) as a template, genes frd1 (corresponding to a gene cg3223 of *C. glutamicum* ATCC13032) and frd2 (corresponding to a gene cg1150 of the *C. glutamicum* ATCC13032) for encoding the hypothetic NADPH-dependent FMN reductases were subjected to primer amplification by using a PCR method by taking a genome of *C. crenatum* SDNN403 (namely *Corynebacterium crenatum* CGMCC NO.0890) as a template, and primer sequences were as follows (nucleotide sequences were respectively shown as SEQ ID NO:5-SEQ ID NO:8):

```
28a-frd1F:  CCGGAATTCATGAAAATCGGCGTCATTCTAG 28a-frd1R:  CCGCTCGAGTTAATCGCGGACAGCCGTTAGGAGGC 28a-frd2F:  CCGGAATTCATGAGCAAGATCGCCATCATCAC 28a-frd2R:  CCCAAGCTTTTAGACGTTTGCAGACTC
```

Recombinant strains BL21/pET-28a-frd1 and BL21/pET-28a-frd2 were obtained by connecting the obtained frd1 and frd2 gene fragments with pET-28a linearized plasmids, transforming *E. coli* BL21 by heat shock and selecting positive transformants. The recombinant strains BL21/pET-28a-frd1 and BL21/pET-28a-frd2 were induced to overexpress target proteins Frd181 and Frd188. The target proteins Frd181 and Frd188 were obtained by nickel column affinity chromatography purification after ultrasonic cell breakage.

The target proteins Frd181 and Frd188 were obtained by nickel column affinity chromatography purification, the purification conditions of the proteins were analyzed by virtue of SDS-PAGE, and the result showed that the purification effect was relatively good.

Functional Identification Carried Out on Proteins Frd181 and Frd188

A reaction system: 0.1M of pH7.5 Tris-HCl, 75 μM of NAD(P)H, 50 μM of flavin (FMN, FAD and riboflavin) and a proper quantity of enzyme liquid. The consumption condition of NAD(P)H was monitored by measuring the change of OD340. Meanwhile, the production condition of $H_2O_2$ in the reaction system was measured by using a phenol red-horseradish peroxidase method and a biological sensor.

A result of functional identification on Frd181 and Frd188 showed that Frd181 was capable of oxidizing NADPH in the existence of FMN and FAD, was capable of oxidizing NADH in the existence of FMN, FAD and riboflavin, and had very high NADH oxidation activity in the existence of FAD and riboflavin. The $H_2O_2$ production analysis shows that $H_2O_2$ was produced in each of catalytic reaction systems of Frd181 and Frd188. The foregoing results showed that Frd181 and Frd188 were NAD(P)H-dependent flavin reductases producing $H_2O_2$.

Example 2: Construction of Gene Knocked-Out Strain

By taking the genome of the *C. crenatum* SDNN403 as a template, frd1 and frd2 gene deletion fragments were obtained by using an overlap extension PCR method, and primer sequences were as follows (nucleotide sequences were respectively shown as SEQ ID NO:9-SEQ ID NO:16):

```
Δfrd1-1:
CCGGAATTCATGAAAATCGGCGTCATTCTAG

Δfrd1-2:
GTTGGCAGCACCTGGAACAGTGG

Δfrd1-3:
CCACTGTTCCAGGTGCTGCCAACGAAGGTGTCCGTGCTGTTGAGCAG

Δfrd1-4:
CTAGTCTAGATTAATCGCGGACAGCCGTTAGGAGGC
```

-continued

Δfrd2-1:
CCGGAATTCATGAGCAAGATCGCCATCATCAC

Δfrd 2-2:
CTGGCATTGCTTCGTCGAG

Δfrd2-3:
CTCGACGAAGCAATGCCAGCAGATCGCACACGTTC

Δfrd2-4:
CCCAAGCTTTTAGACGTTTGCAGACTC

Plasmids pK18mobsacB-Δfrd1 and pK18mobsacB-Δfrd2 were constructed by connecting the obtained frd1 and frd2 gene deletion fragments with pK18mobsacB linearized vectors, shifting to *E. coli* JM109 and selecting positive transformants.

The plasmids pK18mobsacB-Δfrd1 and pK18mobsacB-Δfrd2 were subjected to electric shock to transform the *C. crenatum* SDNN403, a solid culture medium plate containing LBG+Km was coated with the *C. crenatum* SDNN403 after 1800V electric shock was carried out for 5 ms, the *C. crenatum* SDNN403 was cultured at 30° C. for 24-36 h, and then, first homologous recombinant transformants grew. Then, target transformants were respectively subjected to forced secondary recombination screening in a culture medium containing saccharose, finally, streaking was carried out on an LBG plate, several transformants were selected, and strains subjected to second homologous recombination were subjected to wild-type/gene deleted-type restoration identification by PCR. The strains identified to be correct were respectively named as 403Δfrd1 and 403Δfrd2. A strain 403Δfrd12 was obtained by further knocking out the gene frd2 in the strain 403Δfrd1.

Example 3: Influences of Frd1 or Frd2 Gene Knockout to Synthesis of L-Arginine

403Δfrd1, 403Δfrd2 and 403Δfrd12 were subjected to flask shaking fermentation. Fermentation culture medium components: 120 g·L$^{-1}$ of glucose, 40 g/L of corn steep liquor, 8*10-5 g·L$^{-1}$ of biotin, 5*10-4 g·L$^{-1}$ of histidine, 0.02 g·L$^{-1}$ of manganese sulfate, 20 g·L$^{-1}$ of ammonium sulfate, 0.5 g·L$^{-1}$ of magnesium sulfate, 1.5 g·L$^{-1}$ of monopotassium phosphate and 0.02 g·L$^{-1}$ of ferrous sulfate. The fermentation temperature was 30 DEG C., and the rotating speed of a shaking table was 220 r·min$^{-1}$. After being fermented for 60 h, the strains 403Δfrd1, 403Δfrd2 and 403Δfrd12 respectively produce 18.4 g·L$^{-1}$ of L-arginine, 16.3 g·L$^{-1}$ of L-arginine and 18.7 g·L$^{-1}$ of L-arginine.

Comparative embodiment: the *C. crenatum* SDNN403 was subjected to flask shaking fermentation, and fermentation culture medium components and fermentation conditions were the same as those of the embodiment 3. After fermentation for 60 h, the yield of L-arginine was 15.8 g·L$^{-1}$.

The data proved that the L-arginine yield of the strain could be respectively increased by 16.46% and 3.16% by knocking out the gene(s) frd1 and/or frd2.

What is claimed is:

1. A recombinant strain of *Corynebacterium* crenatum comprising a gene knockout of NADPH-dependent flavin mononucleotide (FMN) reductase gene frd1, or frd2, or both frd1 and frd2.

2. The recombinant strain of the *Corynebacterium* crenatum of claim 1, wherein amino acid sequences of the NADPH-dependent FMN reductase genes frd1 and frd2 are respectively amino acid sequences of SEQ ID NO:2 and SEQ ID NO:4.

3. The recombinant strain of the *Corynebacterium* crenatum of claim 1, wherein the recombinant strain of the *Corynebacterium* crenatum is obtained by knocking out NADPH-dependent FMN reductase genes in *Corynebacterium* crenatum CGMCC NO:0890.

4. The recombinant strain of the *Corynebacterium* crenatum of claim 1, wherein nucleotide sequences of the NADPH-dependent FMN reductase genes frd1 and frd2 are respectively nucleotide sequences of SEQ ID NO:1 and SEQ ID NO:3.

5. A method for synthesizing L-arginine, comprising culturing a recombinant strain of *Corynebacterium* crenatum of claim 1 as a production strain.

6. The method of claim 5, wherein:

the culturing step is performed at a temperature of 28° C. to 32° C.; and the culturing step is performed in a medium comprising:

120 g/L glucose, 40 g/L corn steep liquor, $8\times10^{-5}$ g/L biotin, $5\times10^{-4}$ g/L histidine, 0.02 g/L manganese sulfate, 20 g/L ammonium sulfate, 0.5 g/L magnesium sulfate, 1.5 g/L monopotassium phosphate, and 0.02 g/L ferrous sulfate.

7. A method for promoting synthesis of L-arginine by knocking out flavin reductases, comprising:

knocking out NADPH-dependent FMN reductase genes frd1, or frd2, or both frd1 and frd2 in *Corynebacterium* crenatum to obtain a recombinant strain, and synthesizing L-arginine by culturing the recombinant strain as a production strain.

8. The method of claim 7, wherein amino acid sequences of the NADPH-dependent FMN reductase genes frd1 and frd2 are respectively amino acid sequences of SEQ ID NO:2 and SEQ ID NO:4.

9. The method of claim 7, wherein the *Corynebacterium* crenatum is *Corynebacterium* crenatum CGMCC NO:0890.

10. A method of use of the recombinant strain of the *Corynebacterium* crenatum of claim 1 to medicines, food or feed industry, comprising culturing the recombinant strain of *Corynebacterium* crenatum, and synthesizing L-arginine from a culture thereof.

* * * * *